United States Patent [19]

Revus et al.

[11] Patent Number: 4,764,718
[45] Date of Patent: Aug. 16, 1988

[54] MICROWAVE OIL SATURATION SCANNER

[75] Inventors: David E. Revus, Yorba Linda; Russell E. Boyer, Fullerton, both of Calif.

[73] Assignee: Chevron Research Company, San Francisco, Calif.

[21] Appl. No.: 855,539

[22] Filed: Apr. 23, 1986

[51] Int. Cl.$^4$ ............................................. G01N 22/00
[52] U.S. Cl. ........................... 324/58.5 A; 73/61.1 R; 324/58.5 R
[58] Field of Search ..................... 324/58.5 R, 58.5 A, 324/58 A; 73/61.1 R; 250/301

[56] References Cited

U.S. PATENT DOCUMENTS

| | | | |
|---|---|---|---|
| 3,586,971 | 5/1971 | Bosigio | 324/58.5 C |
| 3,644,826 | 2/1972 | Cornetet, Jr. | 324/58.5 A |
| 3,818,333 | 6/1974 | Walker | 324/58.5 A |
| 4,107,993 | 8/1978 | Shuff et al. | 324/58.5 R |
| 4,167,736 | 9/1979 | Tomlinson | 343/5 NA |
| 4,196,385 | 4/1980 | Vestegaard et al. | 324/58.5 B |
| 4,289,020 | 9/1981 | Paap | 73/61.1 R |
| 4,301,400 | 11/1981 | Paap | 324/58.5 A |
| 4,352,288 | 10/1982 | Paap et al. | 73/61 R |
| 4,381,485 | 4/1983 | Steinbrecher | 324/58.5 R |
| 4,423,623 | 1/1984 | Ho et al. | 73/61 R |
| 4,486,714 | 12/1984 | Davis, Jr. et al. | 324/58.5 A |
| 4,490,676 | 12/1984 | Davis, Jr. et al. | 324/376 |
| 4,503,384 | 3/1984 | Nagy et al. | 324/61 |
| 4,519,982 | 5/1985 | Davis, Jr. et al. | 422/68 |
| 4,543,821 | 10/1985 | Davis, Jr. | 73/153 |
| 4,651,085 | 3/1987 | Sakurai et al. | 324/58.5 A |

OTHER PUBLICATIONS

L. A. Davis, Jr., "VHF Electrical Measurement of Saturations in Laboratory Floods", SPE of AIME (SPE 8847).

Primary Examiner—Reinhard J. Eisenzopf
Assistant Examiner—Robert W. Mueller
Attorney, Agent, or Firm—S. R. LaPaglia; E. J. Keeling; V. A. Norviel

[57] ABSTRACT

The present invention is comprised of a non-intrusive microwave sensor system for measuring fluid saturation or multiple fluids contained within a flowline or a fluid saturated porous medium. Here, the microwave oil saturation scanner (MOSS) comprises a transmit portion and a measurement portion. The transmit portion generates two signals for different purposes. The first signal is used as a reference signal upon which the sample signal is eventually compared. The second signal is transmitted through the sample which causes a phase angle shift and signal attenuation. The two signals are then compared in the measurement portion where the phase angle shift and the signal attenuation is related to the concentration of oil and water in the sample mixture.

6 Claims, 2 Drawing Sheets

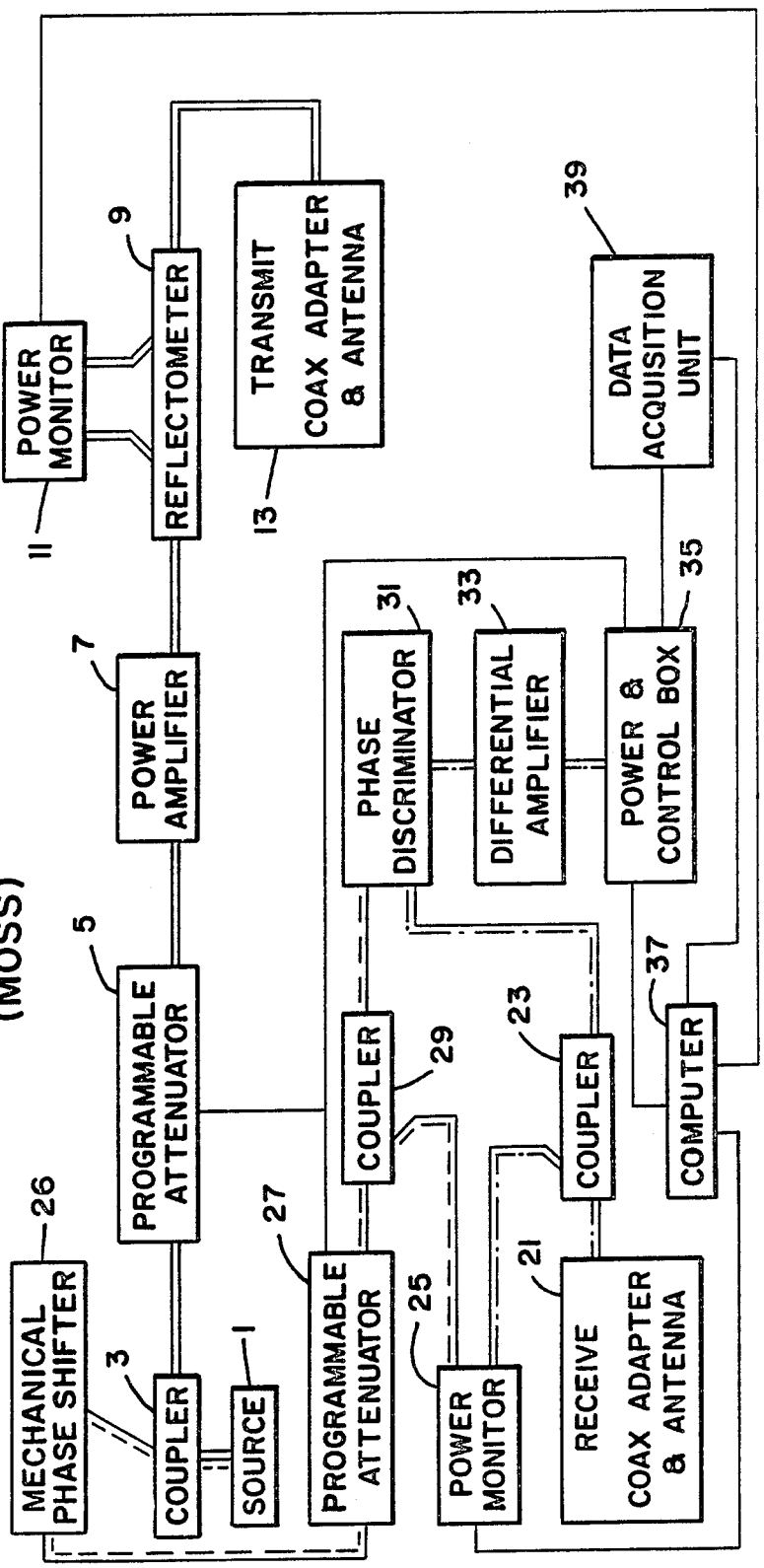

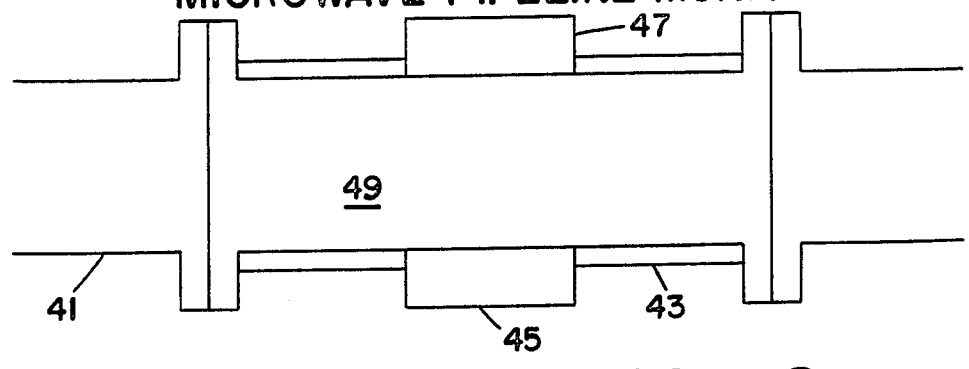
FIG_2
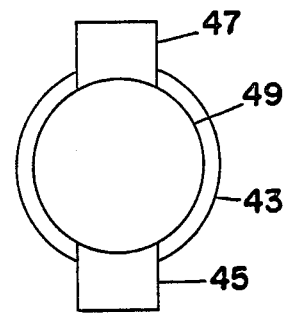
FIG_2a
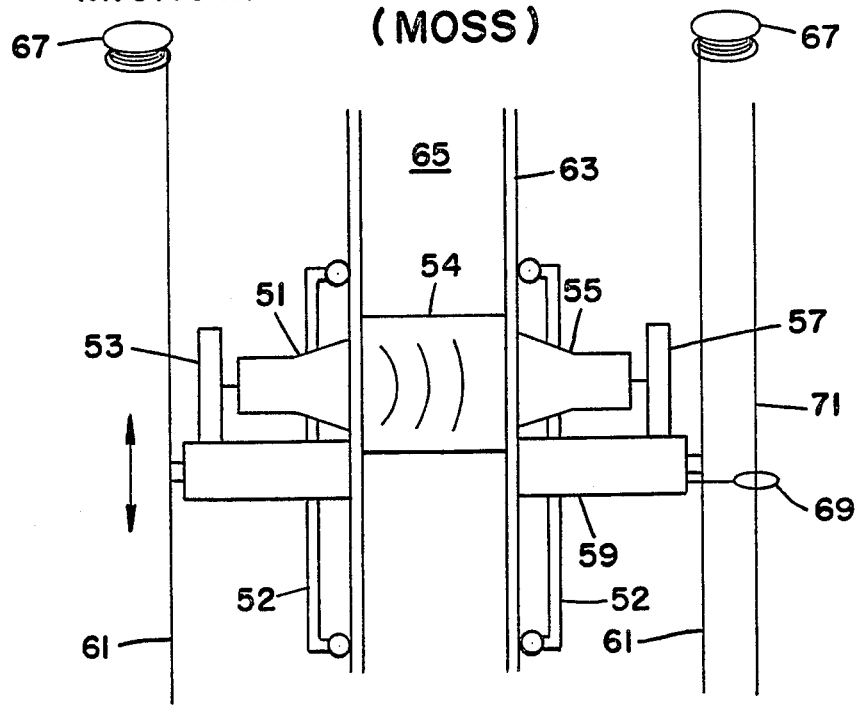
FIG_3

MICROWAVE OIL SATURATION SCANNER

BACKGROUND OF THE INVENTION

1. Field of the Invention

This invention generally relates to the measurement of a multiple phase flow. Here, microwave radiation is used to measure the two-phase fluid content of oil field flowlines and also the two-phase fluid content of fluid-saturated porous media.

2. Background Information

A multiple fluid mixture has at least one physically distinct and mechanically separable fluid within at least one other physically distinct and mechanically separable fluid in a physical/chemical system. In the case at hand a multiple fluid mixture would be something such as a combination of water and oil.

Some of the factors that complicate the measurement of the multiple fluid mixture are: whether the mixture is in a static or dynamic state; and whether the method is intrusive or non-intrusive. One simple method of analyzing a multiple fluid mixture involves capturing of a sample volume of the mixture and then analyzing it (or simply allowing the mixture to separate into its component phases). This method, however, is an intrusive one and involves too much time and effort to capture a sample volume. Furthermore, when captured, there is no guarantee that the sample volume is an adequate representation of the entire sample. If so, the calculation for the total concentration of the two components in the mixture will be erroneous. For that reason a non-intrusive method would be preferable.

Multiple fluid mixtures may also be measured by subjecting a sample (either in a static or dynamic state) to photonic laser, or infra-red radiation. In these cases, a multiple fluid mixture is subjected to the specific radiation and the attenuation of the radiation is used to calculate the component phases. See U.S. Pat. Nos. 4,157,470 to Kotuka et al.; 4,470,647 to Chraphyvy et al.; and 4,394,575 to Nelson; see also V. E. Shrock, "Radiation Attenuation Techniques in Two-Phase Flow Measurements", Nat'l ASME/AICHE, Heat Transfer Conference, Minneapolis (1969); and Davis, "VHF Electrical Measurement of Saturations in Laboratory Corefloods", SPE 8847 (1980).

The other factor that was mentioned above, i.e., whether the mixture is in a static or a dynamic state, would reflect mainly on the particulars of the measurement system. For example, in most applications it is most desirable to measure the mixture when it is in a fluid or flowing state. A common example would be an oil field flowline pipe that may transport liquid. However, there are examples where it may be desirable to measure multiple fluids in a static system. For example, a laboratory situation may be set up in which a sample petroleum formation, containing a porous medium (such as Berea Sandstone), has a two-phase mixture. Both cases could be applications of the same measurement technique.

The techniques described above are useful in understanding how fluid concentrations may be measured in a multiple fluid mixture. However, as applied to petroleum applications, i.e., multiple fluid mixtures of water and oil in a flowline or a test core, microwaves work to distinguish between multiple fluids. Some work has already been done in which microwaves are used to determine the concentration of multiple fluids, as outlined below. The devices disclosed in U.S. Pat. Nos. 4,167,736 to Tomlinson; 4,196,385 to Vesterpaard et al.; 4,423,623 to Ho et al.; and 4,503,384 to Nagy et al. all are intrusive into the fluid that they are measuring and are undesirable because of that fact. U.S. Pat. Nos. 4,289,020 and 4,301,400, to Paap, show devices that manipulate the fluid channel through which crude oil flows and are undesirable because they contain "dead spaces" where the flow may eddy and throw off the measurement system. U.S. Pat. No. 3,586,971 to Besido shows a device that monitors the moisture content in the sheets of material. It uses a method that detects a resonant frequency shift only. U.S. Pat. No. 3,818,333, to Walker, shows a microwave window and antenna, but does not disclose how measurements are made to determine fluid content. The following patents are issued to Lorne A. Davis et al. U.S. Pat. No. 4,519,982 discloses a device that scans a two-dimensional sample. U.S. Pat. Nos. 4,482,634 and 4,490,676 disclose a method ('634) and an apparatus ('676) for monitoring fluid in a core of material. However, both patents only measure power level, not phase shift. U.S. Pat. Nos. 4,486,714 and 4,543,821 use microwave circuitry that is similar to 4,482,634, but show different methods of fluid delivery to a test core. Two articles relate to some of these patents and are: Haskin and Davis, "A Comparison of Laboratory Linear and Pattern Flow Chemical Floods Using a Volumetric Linear Scaling Concept for Oil Saturation and Distributions", SPE 10197 (1981) (see U.S. Pat. No. 4,519,982); Brost and Davis, "Determination of Oil Saturation and Distributions in Field Cores by a Microwave Spectroscopy", SPE 10110 (1981) (see U.S. Pat. Nos. 4,482,634 and 4,490,676).

Other articles disclose the use of microwaves to measure fluid contents. R. W. Parsons was one of the first investigators to disclose a method to determine in situ saturations of multiple fluid phases in a laboratory coreflood using microwave attenuation, see Parsons, "Microwave Attenuation—A New Tool for Monitoring Situations in Laboratory Flooding Experiments", Soc. Pet. Eng. Jour. 302 (August, 1975). However, the signal penetration depth in this method is limited to one inch and the frequency is 21.26 Gigahertz. P. E. Baker discusses a similar method (at the end of the Parsons' paper, see page 309). Bentsen and Saeedi show a method that is similar to Parsons, see Bentsen and Saeedi, "Liquid-Immiscible Displacement in Unconsolidated Porous Media", Jour. Can. Pet. Tech. 93 (January–March, 1981). Their method measures only microwave attenuation, has a penetration depth of only 1.27 centimeters, and operates on a microwave frequency of 27 Gigahertz. Wasan et al. also show a method similar to Parsons, see Wasan et al., "Microwave Spectroscopy Analysis of Surfactant/Polymer Flooding: Interrelationships Between Chemical Slug Properties, Coalescence Phenomena, and Tertiary Oil Recovery", SPE 8327 (1979). For example, Wasan et al. measure microwave attenuation using a frequency of 21.83 Gigahertz. Another similar device is described in Gladfelter and Gupta, "The Effect of Fractional Flow Hysteresis on Recovery of Tertiary Oil", Soc. Pet. Eng. Jour. 509 (December, 1980). Here, measurements of multiple fluids are made with microwave attenuation and depth penetration is limited to 1.91 centimeters. An article that reviews all the current methods to measure multiple fluids and petroleum applications is Saraf, "Methods of In-situ Saturation Determination During Core Tests Involving Multiphase Fluid Flow", Report 1981-6 Petroleum Recovery Institute (March, 1981).

These references mostly use only one measurement technique, i.e., signal attenuation, to determine fluid concentrations. This has some drawbacks, in that: some physical properties are masked in different flow regimes when you use signal attenuation; you may be limited to determining the concentrations of only two fluid phases (with one measurement technique); and you do not have a confirmation of the fluid concentrations when you use a single method.

SUMMARY OF THE INVENTION

A microwave signal is transmitted through a cross section of a non-metallic flowline or a porous medium to determine the concentration of multiple fluids within a sample that is contained in either object. The microwave signal undergoes attenuation and phase angle shift due to the saturation contents of the fluids contained within the sample. These two properties are measured by a microwave receiving assembly which is positioned on one side of the multiple fluid sample, diametrically opposed to a microwave transmitting assembly. A calibration technique relates the fluid saturations to the microwave signal attenuation and phase angle shift measurements. For example, multiple fluids having sufficiently different dielectric constants, such as oil and water, may be combined in known quantities to present a linear calibration curve for comparison with the unknown samples. After comparison of the test result of the unknown sample with a calibration curve, the concentration of the different fluid phases in the sample may be determined.

The present invention is called a Microwave Oil Saturation Scanner and it contains a transmit portion and a measurement portion. Within the transmit portion, there is a microwave source and a microwave transmitting antenna. In the measurement section, there is a receiving antenna, a phase discriminator, and a power level indicator to measure the received signal. Also connecting the two portions is a reference branch which compares the original microwave signal with the signal that has been passed through the sample and then received by the measurement portion.

Though the specification of the present invention uses the term "microwave" to describe the signals generated and analyzed, it is understood that the present invention may generate signals and operate at frequencies outside the frequency band usually considered as microwave.

BRIEF DESCRIPTION OF THE DRAWINGS

FIG. 1 is a schematic representation of a Microwave Oil Saturation Scanner;

FIG. 2 is a side, cross-sectional, diagrammatic view of a microwave pipeline monitor;

FIG. 2a is a front, cross-sectional, diagrammatic view of the device in FIG. 2; and FIG. 3 is a side, cross-sectional, diagrammatic view of a microwave oil saturation scanner that may be used to travel up and down a column of a porous medium.

DETAILED DESCRIPTION OF THE INVENTION

The present invention may be applied to any dynamic or static flowline measurement of a multiple fluid mixture. Initial application of the invention was to measure oil/water concentrations but, any two fluids having sufficiently different dielectric constants may be distinguished (for example, water has a dielectric constant of approximately 80 and oil has a dielectric constant of approximately 2). Here, the concentration of the multiple fluids is determined by relating microwave signal attenuation and phase angle shift to known values. The use of both techniques: provides a verification for each technique; confirms if certain flow phenomena are real or simply masked (e.g., results for signal attenuation may be thrown off if a "slug" of water passes the detector); and may provide analysis for more complex flow systems (two measurement techniques may determine the concentration of three fluid phases). For example, three separate fluid components may be deduced by the simultaneous measurement of microwave phase angle shift and signal attenuation. In a coreflood (i.e., porous medium 65) containing oil, water, and gas, the attenuation permits distinguishing liquids and gas while the degree of phase angle shift of the microwave radiation permits distinguishing the oil and the water.

Microwave Oil Saturation Scanner

Now, referring to the Drawings, FIG. 1 discloses a schematic representation of a Microwave Oil Saturation Scanner (MOSS). The MOSS has two portions, a transmit I and a measurement portion II. Within the transmit portion I there is a source 1 of microwave radiation which is then connected to a coupler 3. The coupler 3 is connected to a programmable attenuator 5 (and also a mechanical phase shifter 26 in the reference branch). The programmable attenuator 5 is connected to a power amplifier 7, a reflectometer 9, and a power monitor 11. (MOSS has a variable power output amplifier to keep the received signal strength within operating limits so that deeper penetration is possible. This is important when the signal attenuation changes drastically during the experiment, such as with brine-oil floods.) The reflectometer 9 is then connected to the means to transmit the microwave signal 13, which has a coax adaptor and an antenna. The measurement portion II comprises a means to receive the microwave signal 21 which also has a coax adaptor and an antenna. (The antenna types for the transmitter and receiver include coax to waveguide adaptors with either microwave horns or resonant slot terminated waveguides, end-fire rod antennas with 45° signal deflectors, and open and closed ended ridged waveguides. Ridged waveguide antennas may provide a better signal coupling and reduce errors due to signal bypassing around the sample.) A coupler 23 is attached to the receiving means 21 and from the coupler 23 there is a power monitor 25 and a phase discriminator 31. The power monitor 25 is connected to a coupler 29 and then to a programmable attenuator 27. As mentioned previously, a mechanical phase shifter 26 is attached to coupler 3 from the transmit portion I and then to a programmable attenuator 27. A phase discriminator 31 is attached to both coupler 23 and coupler 29. (A reference branch III is comprised of coupler 3, mechanical phase shifter 26, programmable attenuator 27, coupler 29, power monitor 25, and phase discriminator 31.) From the phase discriminator 31, a differential amplifier 33 is attached, along with a power and control box 35. Connected to power and control box 35 is a computer 37 and a data acquisition unit 39.

The operation of MOSS is as follows. The microwave signal originates at microwave source 1 and is sent to the coupler 3 that feeds both the reference branch III and the transmit portion I. The microwave source 1 may be operated at 2.45 Gigahertz (although it is not functionally necessary to be limited to this frequency only), which is an ISM frequency approved for use by the United States Federal Communications Commission. We find that for a 6-inch sample, a frequency of 0.915 Gigahertz works well (to determine the proper frequency, see the following section entitled "Frequency Selection"). The coupler 3 splits the signal from the source 1 into two signals. A stronger, transmit signal goes to programmable attenuator 5 and a weaker, branch signal goes to the mechanical phase shifter 26 and the programmable attenuator 27 of the reference branch III. The incident power (i.e., that power which enters the reflectometer 9) is controlled by the programmable attenuator 5 at the input of the power amplifier 7. The transmit signal from the power amplifier is passed to the reflectometer 9 which measures the incident power and the reflected power (that power that is reflected back from the cable that connects the reflectometer 9 to the means for transmitting the signal 13 through the sample). The device that measures the power from the reflectometer 9 is the power monitor 11 which measures the power in decibels (monitor 11 determines the amount of power that is sent out the transmitting means 13 and through the sample). The transmit means 13 then sends the microwave signal out of the transmit portion I of MOSS and through the sample where it undergoes attenuation and phase angle shift. Thereafter, it is picked up at the microwave receiver 21. From here, this received transmit signal is sent to the coupler 23 which splits off a specific percentage of the signal to a power monitor 25 which monitors the level of power received. To determine signal attenuation, the power monitor 25 measures the transmit signal (that has been received at the receiver 21) and then the computer 37 compares it to the transmit signal that is measured at the power monitor 11. This is done before the signals enter the phase discriminator 31 as these two signals must be within operating limits of the phase discriminator 31 (some equipment only allows a 1–6 decibel difference in power between the two signals).

To complete the series of measurements, the phase discriminator 31 measures the phase difference between the two signals (i.e., the branch signal [which has not passed through the sample] and the received transmit signal [which has passed through the sample]) in degrees. This happens when the reference signal arrives from the coupler 29 and the received transmit signal arrives from the coupler 23. However, before the difference in phase (due to the sample) may be measured, the phase angle shift due to the difference in the unequal electrical lengths between the reference and transmit circuitry must be nulled out. To do this, a mechanical phase shifter 26 is placed upstream of the reference branch's programmable attenuator 27. This mechanical phase shifter 26 equalizes the artificial difference in phase angle between the transmit and reference signals and is set during the calibration of MOSS. After the phase angle shift is determined, both it and signal attenuation may be related to the concentration of each fluid component.

The signal, after it leaves the phase discriminator 31, is passed to the differential amplifier 33 which amplifies the signal and then passes it to the power and control box 35. This power and control box 35 acts as the junction for many of the different devices in the system. Obviously, power must be supplied to different devices for them to function and the interaction of several of the devices must be monitored. To assist in this monitoring task is a computer 37, and a data acquisition unit 39. The data acquisition unit provides an interface between the MOSS and the computer 37. The computer, in conjunction with the data acquisition unit, controls all the electronic and mechanical devices within MOSS.

The MOSS can be accurately calibrated for both signal attenuation and phase shift for multiple fluid concentrations by taking microwave attenuation and phase angle shift measurements on a number of oil/water standard mixtures within the sample medium. For example, oil/water mixtures, with concentrations of oil ranging from 0% to 100% and water from 100% to 0%, should be made and run through the system to provide points for a linear calibration curve. Once a sample measurement is taken, it can be related directly to the calibration curve. Measurements may be more accurate and reliable since the actual fluids under investigation are used in the calibration procedure.

Frequency Selection

The selection of the frequency for the MOSS device is partially dependent on sample depth penetration. This is because you want to prevent a phenomenon called "phase wrap". In phase wrap, the phase signal may change its sign which causes an ambiguity in the number of actual degrees of rotation, i.e., $+1$ to $-179$ degrees. The maximum depth of penetration, without phase wrap, can be calculated from the wavelength of the frequency that has been selected, and conversely the frequency may be determined by the depth of penetration that is desired. To determine either factor, you must make sure that one-half of the wavelength (frequency) should not be greater than the electrical length of the sample.

Salinity gradients also affect the selection of the operating frequency because they cause a shift. To determine the optimum frequency for a given salinity, you must find the point where the shift in frequency is the lowest. Here, a balance is struck between a higher frequency, which is less affected by salinity—but has a lower sample penetration, and a lower frequency, which has a higher penetration—but is more affected by salinity. As mentioned before, the operating frequency for the device described above is 0.915 Gigahertz for a 6-inch sample.

MOSS Pipeline Monitor

FIGS. 2 and 2a show a microwave pipeline monitor. FIG. 2 is a diagram illustrating the specific application of the MOSS for an oil/water pipeline. In this application, there is oil field flowline 41 which is normally a metallic (steel) pipe approximately 6 to 8 inches in diameter. Since the microwave radiation will not penetrate a metallic pipe, a non-metallic spool piece 49 (such as fiberglass), is tied into the metallic pipeline 41. (An alternative method is to install non-metallic sensing segments into the metallic pipeline 41.) On this spool piece 49 a microwave transmitting antenna 47 is mounted diametrically opposed to a microwave receiving antenna 45. An electromagnetic shield 43 is placed around the spool piece to prevent outside microwave interference from entering the spool piece 49; and also to prevent the microwaves that are present inside the spool piece 49 (that originate in the transmitting antenna 47) from radiating into the atmosphere. The electromagnetic shield 43 also performs an absorption function for the microwave radiation from the transmitting antenna 47 to prevent unwanted signal reflections. The metallic type shielding could also be housed within a metallic pipe section for added protection in the event of overpressure condition where the fiberglass spool piece could fracture. To ensure that there is a homogeneous fluid flow through the flowline 41, a mixer (not shown) should be placed upstream of the measuring system. And to get a total concentration of each fluid phase through the flowline 41, the pipeline monitor may be adapted for totalizing the multiple fluids when the flow rate is known.

Totalizing multiple fluids is accomplished by first determining the effective measured volume between the transmitting antenna 47 and the receiving antenna 45. Knowledge of the flow rate indicates the time period of fluid exchange within the effective measured volume. A computer can then take the MOSS readings of the effective measured volume, at the determined time period, to determine the totalized fluid.

The microwave sensor system for the flowline 41 could be run as a remote unit or connected to a computer network for more comprehensive monitoring. Commercial applications include use as a well test monitor on oil production pipelines and lease automatic custody transfer units.

Specific pipeline measurements from the system include: water breakthrough detection; water to oil fractions; and produced water and oil totalizing.

MOSS Coreflood Monitor

FIG. 3 shows an illustration of the microwave oil saturation scanner (MOSS) as applied to a laboratory coreflood experiment. This diagram shows that the MOSS system may measure multiple fluid concentration along the length of a coreflood by mounting the sensors and circuitry on a shuttle. Specific coreflood measurements include oil and water saturation, saturation profiles along the coreflood length, flood front detection, and relative porosity values when the porous media is 100% saturated with water.

The instrumentation of this application of the MOSS is as follows. There is a fluid-saturated porous medium 65 (such as a Berea Sandstone core) that is enclosed by a non-metallic material 63, such as fiberglass. There is a transmitting antenna assembly 51 along with transmit circuitry 53 mounted adjacent to the non-metallic material 63. Diametrically opposed to this material is a receiving antenna assembly 55 along with its associated receive circuity 57. This equipment is movable up and down the non-metallic material 63 on a shuttle car 59 which moves by virtue of a shuttle cable 61. Absorber foam 54 is packed around the non-metallic material 63 and the antennas 51 and 55 to prevent signal bypassing, i.e., electromagnetic signal leakage. The foam is attached to the shuttle car 59 and moves along with the entire assembly. Scanning is achieved when the shuttle car 59 moves up and down the non-metallic material 63 and allows the transmitting antenna assembly 51 to send a microwave signal through the non-metallic material 63 and the fluid-saturated porous medium 65 whereby the (attenuated and phase-shifted) radiation is then picked up by the receiving antenna assembly 55. The shuttle 59 is equipped with profile positioning rollers 52 to provide a centering mechanism with the non-metallic material 63 and to reduce drag during movement. A shunt magnet 69 is mounted on the shuttle and it encircles a position indicator reference tube 71 which is suspended on an adjacent frame (not shown). The position indicator 71 works on a time domain principle. The position of the shunt magnet 69 provides both the reflection point and the position of the shuttle 59 in reference to the porous medium 65. The read out from the position indicator 71 is monitored and controlled by a microcomputer which provides very accurate positioning.

Other devices apparently use stepper motors to position the antenna or core. However, the positive indicating position system that MOSS uses is different from a stepper motor controller. A stepper motor system has no way to read absolute position at all times, it only moves so far for each step pulse from a given point. If the controller fails to reset the antenna to the proper start position one could scan at the wrong positions. The MOSS positioning resolution is accurate within 1/16 inch over 21 feet.

Movement of the shuttle 59 is provided by a single layer drum winch 67 feeding four separate aircraft wire rope cables 61 connected in a closed loop configuration. Tensioning of the cable 61 is provided by four marine turnbuckle assemblies (not shown). The winch 67 can be controlled manually from its own control box or by a microcomputer.

Since many modifications and variations of the present invention are possible within the spirit of this disclosure, it is intended that the embodiments disclosed are only illustrative and not restricted. For that reason, reference is made to the following claims rather than to the specific description to indicate the scope of this invention.

What is claimed is:

1. An apparatus for measuring relative concentrations of oil and water, comprising:
   I. a transmit portion, which comprises:
   (a) a microwave source;
   (b) a first coupler attached to the microwave source to split a microwave signal into a lower strength branch signal and a higher strength transmit signal;
   (c) a first programmable attenuator attached to the first coupler to control a strength of the transmit signal;
   (d) a power amplifier attached to the programmable attenuator to increase the signal strength of the transmit signal to a specific level;
   (e) a microwave transmitting antenna to transmit the transmit signal through a sample;
   (f) a reflectometer and a power monitor attached to the power amplifier and to the microwave transmitting antenna to measure the strength of the transmit signal that is transmitted;
   II. a reception portion, which comprises:
   (a) a microwave receiving antenna to receive the transmit signal after it has passed through the sample;
   (b) a second coupler attached to the receiving antenna to split the received signal into a comparison received signal and a measurement received signal, the comparison received signal weaker and a known fraction of the measurement received signal;
   (c) a power monitor attached to the coupler of Step II(b) to measure and monitor the strength of the total received signal by measuring the comparison received signal and back calculating, this measurement is made so that the strength of the measurement received signal may be regulated;
   III. a reference portion, which comprises:
   (a) a mechanical phase shifter attached to the first coupler of Step I(b) to null out an unwanted phase angle difference caused by unequal electrical lengths in the reference and transmit circuitry;

(b) a second programmable attenuator attached to the mechanical phase shifter to control the strength of the branch signal generated (of Step I(b));

(c) a third coupler attached to the second programmable attenuator (of Step III(b)) to split the signal into a comparison branch and a measurement branch signal, the comparison branch signal is sent to the power monitor (of Step II(c)) for the purpose of calculating the total strength of the branch signal from the second programmable attenuator (of Step III(b)) and to compare the strength of the branch signal to the received signal (of Step II(b));

IV. a calculation portion, which comprises:

(a) a phase discriminator attached to the third coupler (of Step III(c)) and the second coupler (of Step II(b)) to compare and calculate the difference in the phase shift between the measurement branch signal (of Step III(c)) and the measurement received signal (of Step II(b));

(b) means to determine the signal attenuation by comparing the strength of the transmit signal that is transmitted (as measured by the reflectometer and power monitor of Step I(f)) to the strength of the received signal (as measured by the power monitor of Step II(c));

(c) a differential amplifier attached to the phase discriminator to amplify the difference in the branch signal and the received signal; and (d) a power, control, and display means.

2. The device as recited in claim 1 where the frequency of the microwave signal is between 0.5 to 3 Gigahertz.

3. The device as recited in claim 1 where the frequency of the microwave signal is between 0.9 to 2.5 Gigahertz.

4. The device as recited in claim 1 where the frequency of the microwave signal is 0.915 Gigahertz.

5. A device for measuring fluid content in a porous medium, comprising:

(A) a non-metallic material to enclose said porous medium;

(B) means for determining signal attenuation and phase angle shift of a multiple fluid mixture operably mounted on said porous medium, and further comprising:

I. a transmit portion, which comprises:
(a) a microwave source;
(b) a first coupler attached to the microwave source to split a microwave signal into a lower strength branch signal and a higher strength transmit signal;
(c) a first programmable attenuator attached to the first coupler to control a strength of the transmit signal;
(d) a power amplifier attached to the programmable attenuator to increase the signal strength of the transmit signal to a specific level;
(e) a microwave transmitting antenna to transmit the transmit signal through a sample;
(f) a reflectometer and a power monitor attached to the power amplifier and to the microwave transmitting antenna to measure the strength of the transmit signal that is transmitted;

II. a reception portion, which comprises:
(a) a microwave receiving antenna to receive the transmit signal after it has passed through the sample;
(b) a second coupler attached to the receiving antenna to split the received signal into a comparison received signal and a measurement received signal, the comparison received signal weaker and a known fraction of the measurement received signal;
(c) a power monitor attached to the coupler of step II(b) to measure and monitor the strength of the total received signal by measuring the comparison received signal and back calculating, this measurement is made so that the strength of the measurement received signal may be regulated;

III. A reference portion, which comprises:
(a) a mechanical phase shifter attached to the first coupler of Step I(b) to mull out an unwanted phase angle difference caused by unequal electrical lengths in the reference and transmit circuitry;
(b) a second programmable attenuator attached to the mechanical phase shifter to control the strength of the branch signal generated of Step I(b);
(c) a third coupler attached to the second programmable attenuator of Step III(b) to split the signal into a comparison branch and a measurement branch signal, the comparison branch signal is sent to the power monitor of Step II(c) for the purpose of calculating the total strength of the branch signal from the second programmable attenuator of Step III(b) and to compare the strength of the branch signal to the received signal of Step II(b);

IV. a calculation portion, which comprises:
(a) a phase discriminator attached to the third coupler of Step III(c) and the second coupler of Step II(b) to compare and calculate the difference in the phase shift between the measurement branch signal of Step III(c) and the measurement received signal of Step II(b);
(b) means to determine the signal attenuation by comparing the strength of the transmit signal that is transmitted as measured by the reflectometer and power monitor of Step I(f) to the strength of the received signal as measured by the power monitor of step II(c);
(c) a differential amplifier attached to the phase discriminator to amplify the difference in the branch signal and the received signal; and
(d) a power, control, and display means;

(C) means for moving the transmit and reception portions along different portions of the porous medium in a manner such that the transmit and reception portions are always kept in a fixed position relative to one another; and (D) means for determining an exact position of the transmit and reception portions.

6. A microwave laboratory analyzer for use in determining the multiple fluid components in a porous medium, comprising:

(A) a non-metallic material to enclose said porous medium;

(B) a transmit portion operably attached to said non-metallic material, which comprises:

i. a microwave source;

ii. a first coupler attached to the microwave source to split a microwave signal into a lower strength branch signal and a higher strength transmit signal;

iii. a first programmable attenuator attached to the first coupler to control a strength of the transmit signal;

iv. a power amplifier attached to the programmable attenuator to increase the signal strength of the transmit signal to a specific level;

v. a microwave transmitting antenna to transmit the transmit signal through a sample;

vi. a reflectometer and a power monitor attached to the power amplifier and to the microwave transmitting antenna to measure the strength of the transmit signal that is transmitted;

(C) a reception portion mounted diametrically opposed to said transmit portion on said non-metallic material, and further comprising:

i. a microwave receiving antenna to receive the transmit signal after it has passed through the medium;

ii. a second coupler attached to the receiving antenna to split the received signal into a comparison received signal and a measurement received signal, the comparison received signal weaker and a known fraction of the measurement received signal;

iii. a power monitor attached to the coupler of Step (C)ii to measure and monitor the strength of the total received signal by measuring the comparison received signal and back calculating, this measurement is made so that the strength of the measurement received signal may be regulated;

(D) a means to prevent electromagnetic leakage around the porous medium;

(E) a reference portion, which comprises:

i. a mechanical phase shifter attached to the first coupler to null out an unwanted phase angle difference caused by unequal lengths in the reference and transmit circuitry;

ii. a second programmable attenuator attached to the mechanical phase shifter to control the strength of the branch signal;

iii. a third coupler attached to the second programmable attenuator to split the branch signal into a comparison branch and a measurement branch signal, the comparison branch signal is sent to the power monitor for the purpose of calculating the total strength of the branch signal from the second programmable attenuator and to compare the strength of the branch signal to the received signal;

(F) a calculation portion, which comprises:

i. a phase discriminator attached to the third coupler and the second coupler to compare and calculate the difference in the phase shifter between the measurement branch signal and the measurement received signal;

ii. means to determine the signal attenuation by comparing the strength of the transmit signal that is transmitted to the strength of the received signal;

(G) a shuttle car attached to said transmit and reception portions in such a manner that the transmit and reception portions are kept in a fixed position and distance relative to one another;

(H) a shuttle cable connected to said shuttle car for moving the transmitting and receiving assemblies along the surface of said non-metallic material containing said porous medium;

(I) a drum winch for moving the shuttle cable;

(J) profile positioning rollers to keep the transmit and reception portions in a proper position relative to the porous medium;

(K) a shunt magnet mounted on the shuttle; and (L) a position indicator reference means encircled by the shunt magnet.

* * * * *

UNITED STATES PATENT AND TRADEMARK OFFICE
CERTIFICATE OF CORRECTION

PATENT NO. : 4,764,718
DATED : August 16, 1988
INVENTOR(S) : David E. Revus and Russell E. Boyer It is certified that error appears in the above-identified patent and that said Letters Patent are hereby corrected as shown below:

Claim 5 III.(a), Col. 10, Line 19, "to mull out" should read --to null out--.

Claim 6 (F)i, Col. 12, Line 18, "phase shifter" should read --phase shift--.

Signed and Sealed this

Twenty-first Day of March, 1989

Attest:

DONALD J. QUIGG

Attesting Officer

Commissioner of Patents and Trademarks